United States Patent
Mizuno et al.

(10) Patent No.: US 10,955,401 B2
(45) Date of Patent: Mar. 23, 2021

(54) CHEMICAL FOR TEST USED IN HAZARDOUS SUBSTANCE SENSING DEVICE, HAZARDOUS SUBSTANCE SENSING DEVICE, AND HAZARDOUS SUBSTANCE SENSING METHOD

(71) Applicant: Hitachi, Ltd., Tokyo (JP)

(72) Inventors: Hiroki Mizuno, Tokyo (JP); Hisashi Nagano, Tokyo (JP); Takahiro Itou, Tokyo (JP); Makoto Namai, Tokyo (JP); Fumihiko Nemoto, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 226 days.

(21) Appl. No.: 16/309,310

(22) PCT Filed: Apr. 13, 2017

(86) PCT No.: PCT/JP2017/015082
§ 371 (c)(1),
(2) Date: Dec. 12, 2018

(87) PCT Pub. No.: WO2017/217096
PCT Pub. Date: Dec. 21, 2017

(65) Prior Publication Data
US 2019/0178865 A1    Jun. 13, 2019

(30) Foreign Application Priority Data
Jun. 14, 2016    (JP) .............................. JP2016-117580

(51) Int. Cl.
*G01N 33/22*    (2006.01)
*G01N 27/62*    (2021.01)
(Continued)

(52) U.S. Cl.
CPC ............ *G01N 33/227* (2013.01); *G01N 27/62* (2013.01); *H01J 49/422* (2013.01); *H01J 49/4225* (2013.01); *H01J 49/26* (2013.01)

(58) Field of Classification Search
CPC ..... G01N 33/227; G01N 27/62; H01J 49/422; H01J 49/4225; H01J 49/26
See application file for complete search history.

(56) References Cited

U.S. PATENT DOCUMENTS

| 4,409,155 A | 10/1983 | Bonnycastle et al. |
| 7,751,999 B1 | 7/2010 | McAtee et al. |

(Continued)

FOREIGN PATENT DOCUMENTS

| CA | 2904479 A1 * | 9/2015 | .......... H01J 49/0027 |
| CA | 2945544 A1 * | 1/2016 | ............. G01N 21/65 |

(Continued)

OTHER PUBLICATIONS

Chinese-language Office Action issued in Chinese Application No. 201780024019.1 dated Jul. 1, 2020 with English translation (16 pages).

(Continued)

*Primary Examiner* — Jennifer Wecker
*Assistant Examiner* — Jonathan Bortoli
(74) *Attorney, Agent, or Firm* — Crowell & Moring LLP (57) ABSTRACT

In order to suppress malfunctions even when using a reagent (chemical for reagent) corresponding to a hazardous substance, the present invention has an analyzing unit in which a chemical for reagent, having added thereto an indicator that is different from a hazardous material that is a detection target, is used to calibrate on the basis of the detection target included in the chemical for reagent, and which performs mass spectrometry. When a peak corresponding to the indicator is not included and a peak corresponding to the (Continued)

detection target material is included in the spectrum that is the analysis result of the analyzing unit, the detection target is determined to be included.

8 Claims, 8 Drawing Sheets

(51) Int. Cl.
    *H01J 49/42*     (2006.01)
    *H01J 49/26*     (2006.01)

(56) References Cited

U.S. PATENT DOCUMENTS

| | | | |
|---|---|---|---|
| 8,173,959 | B1 | 5/2012 | Boumsellek et al. |
| 8,921,774 | B1 * | 12/2014 | Brown .................... H01J 49/26 250/282 |
| 2001/0042413 | A1 | 11/2001 | Sakairi et al. |
| 2006/0108522 | A1 | 5/2006 | Nagano et al. |
| 2009/0184820 | A1 | 7/2009 | Takada et al. |
| 2009/0224150 | A1 | 9/2009 | Matyjaszczyk et al. |
| 2010/0044557 | A1 | 2/2010 | Prox et al. |
| 2014/0151543 | A1 | 6/2014 | Nagano et al. |

FOREIGN PATENT DOCUMENTS

| | | |
|---|---|---|
| CN | 1162993 A | 10/1997 |
| CN | 101498705 A | 8/2009 |
| CN | 101644686 A | 2/2010 |
| CN | 101949889 A | 1/2011 |
| CN | 103221812 A | 7/2013 |
| CN | 103399075 A | 11/2013 |
| CN | 103512946 A | 1/2014 |
| CN | 103884770 A | 6/2014 |
| CN | 104122298 A | 10/2014 |
| JP | 56-109891 A | 8/1981 |
| JP | 2000-28579 A | 1/2000 |
| JP | 2011-117885 A | 6/2011 |
| WO | WO 2016/003524 A2 | 1/2016 |

OTHER PUBLICATIONS

International Search Report (PCT/ISA/210) issued in PCT Application No. PCT/JP2017/015082 dated Jul. 4, 2017 with English translation (five pages).

Japanese-language Written Opinion (PCT/ISA/237) issued in PCT Application No. PCT/JP2017/015082 dated Jul. 4, 2017 (three pages).

Nakazono, "Taikiatsu Ion-gen o Yusuru Multi Turn Hiko Jikangata Shitsuryo Bunsekikei no Kaihatsu", Osaka University Rigaku Kenkyuka Butsuri Senko Shushi Ronbun, Mar. 2013, p. 21, with unverified partial English translation (two pages).

Extended European Search Report issued in European Application No. 17813002.7 dated Feb. 10, 2020 (eight (8) pages).

\* cited by examiner

| NUMBER OF TIMES OF ADHESION | ADHESION AMOUNT (μg) | NUMBER OF COUNT TNT (m/z 227) | NUMBER OF COUNT DNT (m/z 180) |
|---|---|---|---|
| 1 | 50 | 6.57 E5 | 2.10 E7 |
| 2 | 100 | 1.05 E6 | 3.31 E7 |
| 3 | 150 | 1.31 E6 | 4.35 E7 |
| 4 | 200 | 1.76 E6 | 5.55 E7 |

CHEMICAL FOR TEST USED IN HAZARDOUS SUBSTANCE SENSING DEVICE, HAZARDOUS SUBSTANCE SENSING DEVICE, AND HAZARDOUS SUBSTANCE SENSING METHOD

TECHNICAL FIELD

The present invention relates to a chemical for a test used in a hazardous substance sensing device, a hazardous substance sensing device, and a hazardous substance sensing method.

BACKGROUND ART

A threat of terrorism is globally increased and countermeasures against terrorism due to a hazardous substance such as explosives are required for important facilities such as a nuclear power plant. As a method of manufacturing the explosives using everyday goods is widely known, terrorism and crime due to the explosives are a threat in daily life. Simultaneous multiple terror aimed at subways and buses globally occurred and numerous casualties were reported. In addition, a case such as arresting a suspect who tried suicide bombing inside the commuter train is reported.

As a device for sensing such hazardous substance, there is known a device in which an inspection target is sampled, the inspection target is mass analyzed by applying a mass spectrometry technique, and the fact that the hazardous substance is detected is displayed on a display, when a substance corresponding to an ion of the hazardous substance is detected in a mass analysis result.

Such a technique is described, for example, in JP-A-2000-28579. By using equipment using these techniques, special skill, knowledge, and training are not required for explosive sensing.

CITATION LIST

Patent Literature

PTL 1: JP-A-2000-28579

SUMMARY OF INVENTION

Technical Problem

In routine checking of the soundness of the device, for example, in a trace type hazardous substance sensing device having a mass spectrometer, the operation of the device is confirmed in many cases by inputting a reagent containing the same substance as a hazardous substance. In particular, in a case where the reagent containing the same substance as the hazardous substance is input, the same mass spectrum as the hazardous substance is measured. However, in a case where a hazardous substance reagent is used for operation confirmation, there is a possibility that the hazardous substance reagent may remain in the device. There was a problem that it was impossible to distinguish between erroneous sensing due to the hazardous substance reagent remaining when the hazardous substance was sensed during operation and sensing of the hazardous substance due to a real hazardous substance. As a result, it is expected that the erroneous sensing occurs frequently due to the hazardous substance reagent adhering to a periphery of the device after performing the operation confirmation. In particular, in facilities where thousands or tens of thousands of people go through each day, reduction in throughput due to the erroneous sensing is a big problem, so that it is extremely important to suppress the erroneous sensing by the unnecessary hazardous substance reagent.

Although it is one method to prevent false alarms during operation by confirming the operation of the device by inputting a substance different from the hazardous substance, in order to confirm the reliable performance, it is necessary to confirm the operation of the device by putting the same substance as an inspection target.

In addition, there is a technique of adhering to the inspection target with a pen or the like containing a reagent solution in a normal hazardous substance sensing device. However, there was a problem that it is difficult to adhere the reagent quantitatively to the inspection target.

An object of the present invention is to provide a chemical for a test used in a hazardous substance sensing device, a hazardous substance sensing device, and a hazardous substance sensing method capable of suppressing malfunction even in a case where a reagent (reagent chemical) corresponding to a hazardous substance is used.

Solution to Problem

In the invention, in order to achieve the above object, there is provided a hazardous substance sensing device using a reagent chemical to which an indicator substance different from a hazardous substance as a detection target is added and calibrated based on the detection target included in the reagent chemical, the device including an analysis unit performing mass analysis, and a determination unit determining that the detection target is included, in a case where a peak corresponding to the indicator substance is not included and a peak corresponding to the substance as the detection target is included in a spectrum as an analysis result of the analysis unit.

Alternatively, a chemical for a test of a hazardous substance sensing device, including a hazardous substance as a detection target, and an additional substance as an indicator substance different from the hazardous substance.

Specifically, when the hazardous substance reagent is input to the trace type hazardous substance sensing device having a mass spectrometer used for the hazardous substance sensing, a technique that can distinguish whether the hazardous substance reagent is a real hazardous substance or a remaining hazardous substance reagent is proposed. The trace type hazardous substance sensing device mainly determines the substance contained in an inspection substance from the obtained mass spectrum from the result of generating ions from the inspection substance and performing mass analysis. Therefore, the indicator substance is added to the hazardous substance reagent so that the mass spectrum which does not originally occur in a case where the hazardous substance is inspected is measured. Therefore, even in a case where the hazardous substance reagent is inspected, amass spectrum different from amass spectrum of the hazardous substance is measured, and it can be determined that the inspected substance is the hazardous substance reagent. This technique can be applied not only to a solution but also to solids such as fine particles.

Advantageous Effects of Invention

According to the invention, even in a case where the reagent corresponding to the hazardous substance is used, malfunction can be suppressed.

DESCRIPTION OF EMBODIMENTS

As a mode for performing the invention, a chemical for a test used in a trace type hazardous substance sensing device, an inspection technique, and a detection flow will be described in detail with reference to the drawings.

General Description

First, a basic concept will be described. A mass spectrum of a hazardous substance sensing and amass spectrum of a reagent indicator substance sensing are set in the trace type hazardous substance sensing device, and even in a case where the mass spectrum of the hazardous substance sensing is sensed at the time of inspecting the hazardous substance, in a case where the mass spectrum of the reagent indicator substance sensing is sensed simultaneously, immediately before, or immediately after, a configuration of an alarm condition such as excluding from the alarm condition of the hazardous substance sensing is adopted. Therefore, a chemical for a test is excluded from an alarm and it is possible to prevent erroneous sensing due to the chemical for the test during operation. Therefore, even if the chemical for the test is mistakenly mixed in the operation of the trace type hazardous substance sensing device, it is possible to determine that it is the chemical for the test without determining it as the hazardous substance.

In addition, by adding an indicator substance so that mass spectra of a plurality of indicator substances is measured in the chemical for the test, a plurality of patterns of mass spectra of the hazardous substance reagent can be prepared, and it is possible to prevent illegal carry-in of the hazardous substance due to the determination of the indicator substance. Therefore, by changing a combination of additive substances according to the installation environment and operation situation, even if one pattern of additional substance is specified, it is possible to prevent expansion of illegal carry-in.

Example 1

<System>

Figure 1:
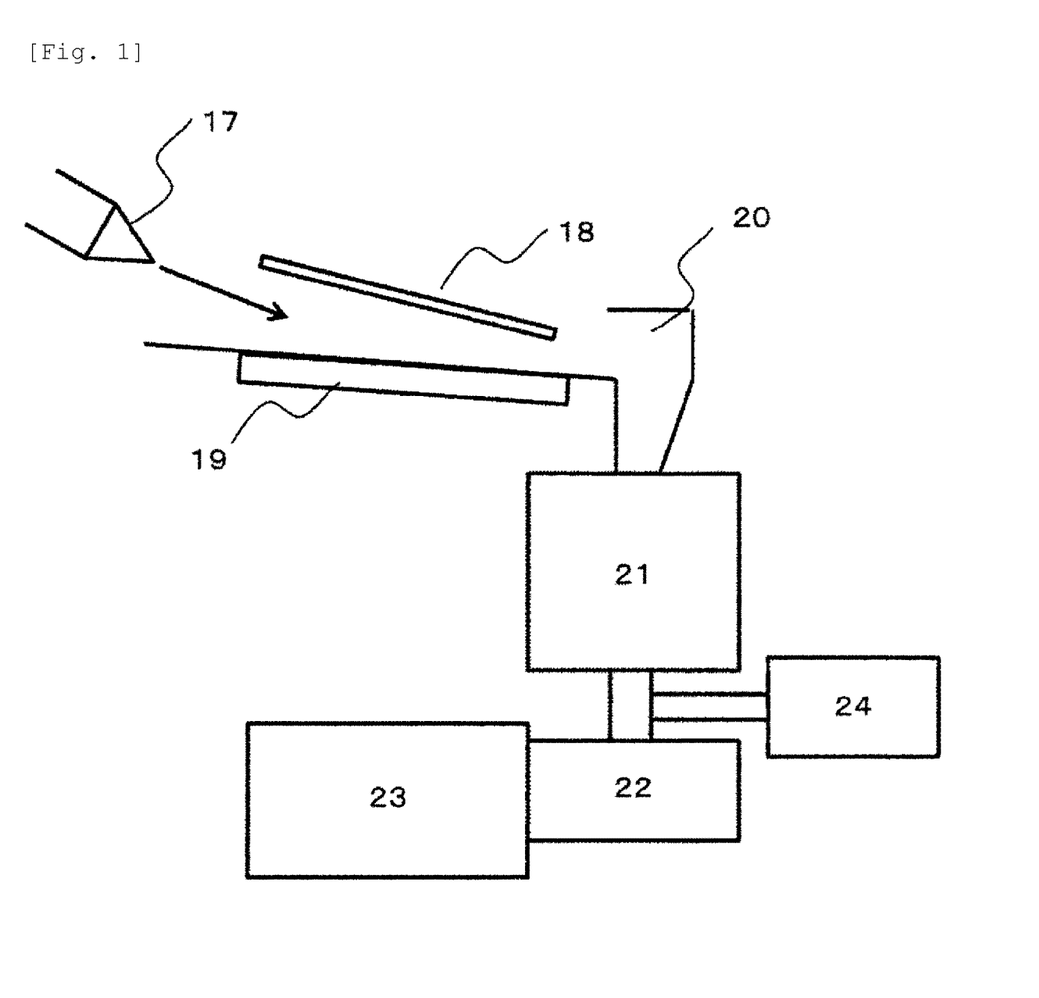
FIG. 1 is a diagram illustrating an example of a configuration of a fine particle inspection device as a trace type hazardous substance sensing device.

An example of a fine particle inspection method as a trace type hazardous substance sensing will be described for an example of the invention. FIG. 1 is a diagram illustrating an example of a configuration of a fine particle inspection device as a trace type hazardous substance sensing device. In FIG. 1, gas and/or fine particles of a detection target substance attached to an inspection target 18 above an authentication unit 19 is separated by an air flow from an air supply unit 17. A separated sample is sucked from a suction port 20, condensed and collected by a fine particle collection unit 21. Ions of the sample are generated by an ion source unit 22, and a mass analysis unit 23 performs mass analysis. A cyclone, a filter, and an impactor may be used for the fine particle collection unit. It is for determining the presence or absence of a mass spectrum derived from the detection target substance from the obtained mass spectrum. In addition, not only an intensity but also a mass axis can be adjusted by the collected sample. A calibrant generator 24 is used for confirming the operation of the device, correcting the intensity of the mass spectrum, or adjusting the mass axis by generating a certain amount of calibration gas by inserting the calibration substance. As an example of a calibration substance, lactic acid, tribromorescorcinol, and bromochlorophenol are used for measurement of negative ions, and 3'-nitroacetophenone is used for measurement of positive ions. In the above description, four types of calibration substances are described as an example, and other calibration substances may be used if a calibration gas is generated. In addition, these calibration substances may be used as dopants. The calibrant generator 24 may be used only by a combination of the ion source unit 22 and the mass analysis unit 23.

In order to confirm the soundness of the device, it is necessary to confirm whether or not the fine particles of the hazardous substance attached to the card can be collected. Therefore, it is desirable for the device in FIG. 1 to inspect whether the reagent can be sensed by inspection flow by attaching a small amount of reagent to the inspection target 18 when checking the soundness.

In the example, a mass spectrometer is used as an explanation. Alternatively, other methods such as a linear ion trap mass spectrometer, a quadrupole ion trap mass spectrometer, a triple quadrupole mass spectrometer, a time-of-flight type mass spectrometer, a magnetic field type mass spectrometer, and an ion mobility mass spectrometer may be used as an analysis method.

<Chemical for Test>

Figure 2:
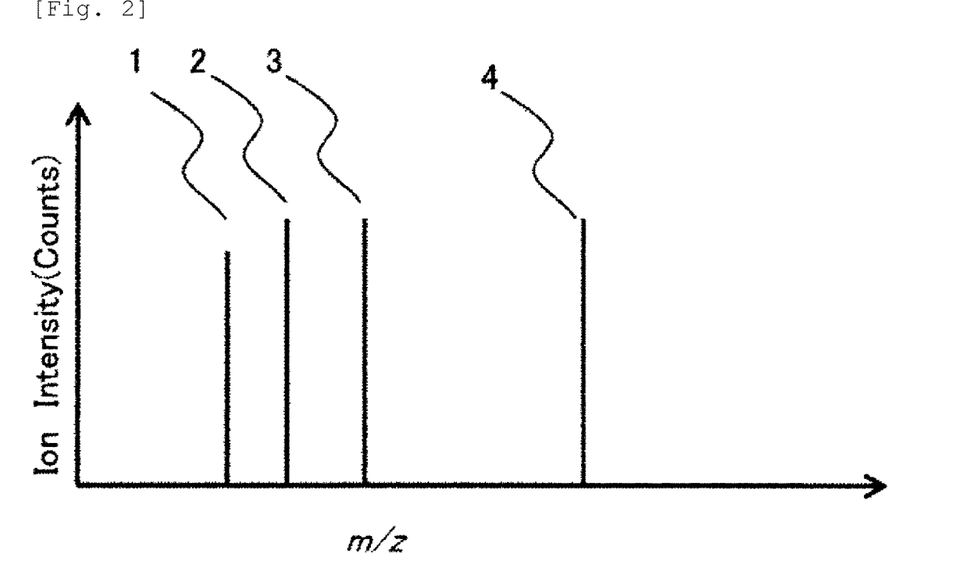
FIG. 2 is a diagram illustrating an example of an outline of a mass spectrum graph.

FIG. 2 is a diagram illustrating an example of an outline of a mass spectrum graph of a chemical for a test (also referred to as reagent) of the invention. The indicator substance is added to the chemical for the test of a hazardous substance A so that the spectrum of peak 4 is sensed simultaneously with the mass spectrum of hazardous substance A as the mass spectrum of the indicator substance.

The chemical for the test is a chemical for a test such that peak 1 (count A1, mass (m/z)=B1), peak 2 (count A2, mass B2), peak 3 (count A3, mass B3), and peak 4 (count A4, mass A4) are output if the fine particle inspection device (trace type hazardous substance sensing device) is in a state that can be analyzed with correct accuracy. Here, the peak 1, the peak 2, and the peak 3 correspond to the components contained in the hazardous substance, and the peak 4 is used as a reagent indicator substance and is a component that is not normally contained in the hazardous substance.

Before identifying the hazardous substance A with the fine particle inspection device, the fine particle inspection device is calibrated using the chemical for the test. That is, in a case where the result of analyzing the chemical for the test with the fine particle inspection device is different from the spectrum illustrated in FIG. 2 in count (amount on vertical axis illustrated in FIG. 2) and mass (amount on horizontal axis illustrated in FIG. 2), the parameters of the fine particle inspection device are adjusted and the parameters are adjusted until the same (or substantially the same) spectrum as the spectrum illustrated in FIG. 2 is output (until (count A1, mass (m/z)=B1), (count A2, mass B2), (count A3, mass B3), and (count A4, mass A4) are output).

<Analysis Operation>

Figure 3:
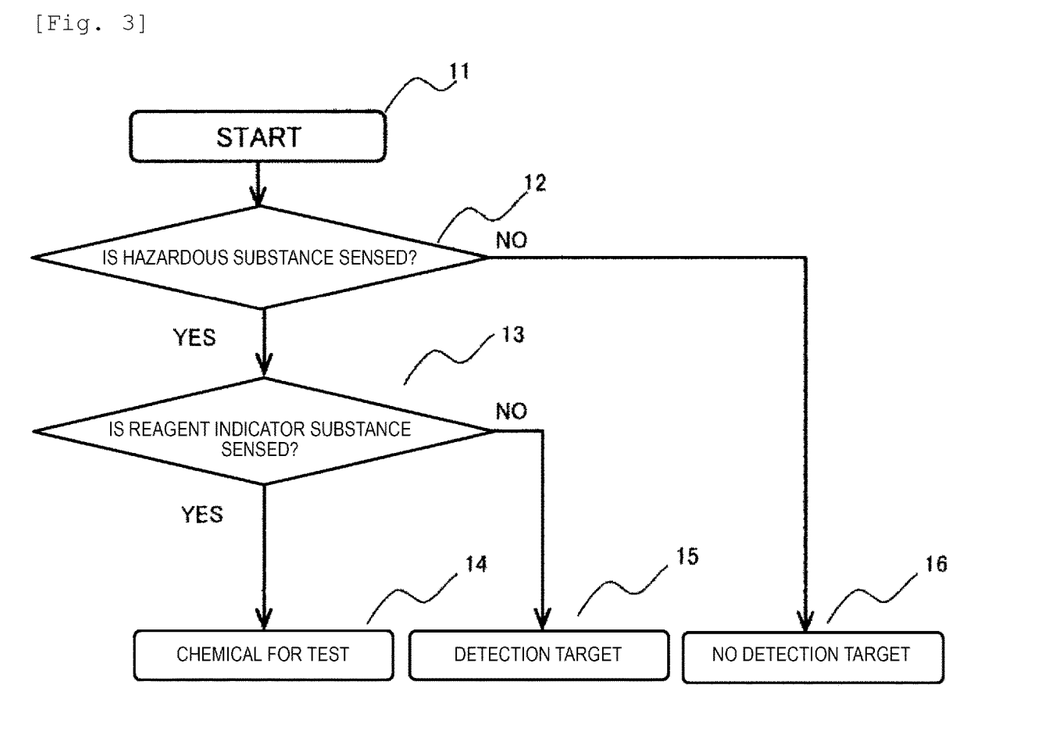
FIG. 3 is a flow illustrating an example of a detection flow of the trace type hazardous substance sensing device.

FIG. 3 is a diagram illustrating an example of a detection flow for distinguishing the chemical for the test from a real explosive. This operation is performed in the mass analysis unit 23 of the fine particle inspection device as the trace type hazardous substance sensing device. That is, the mass analysis unit 23 incorporates an electronic computer and software for operating the electronic calculator, or has the electronic computer and software externally, and the detection flow of FIG. 3 is executed by the software.

In Step 11, the analysis related to the sensing of the hazardous substance A is started. Here, at the start of the analysis, it is premised that the fine particle inspection device is calibrated using the chemical for the test.

In Step 12, it is determined whether or not the hazardous substance A is sensed. In a case where mass spectra 1, 2, and 3 of the hazardous substance in FIG. 2 are sensed as mass spectra when the hazardous substance A is mass analyzed, when the chemical for the test of the hazardous substance A is input to the fine particle inspection device (trace type hazardous substance sensing device), peaks of the mass spectra of the hazardous substance 1, 2 and 3 in FIG. 2 are generated and it is determined as the hazardous substance.

If the hazardous substance A is not sensed in Step 12, it is determined in Step 16 that there is no detection target (hazardous substance A) and the fact of "no detection target" is displayed on a display device (not illustrated). The flow is ended.

If the hazardous substance A is sensed in Step 12, it is determined in Step 13 whether a reagent indicator substance is sensed. That is, it is determined whether the peak 4 in FIG. 2 is detected.

If the reagent indicator substance is not sensed in Step 12, it is determined in Step 15 that the detection target (hazardous substance A) is detected. The fact that there was "detection target" is displayed on the display device (not illustrated). Here, since the peak 4 in FIG. 2 included in the reagent indicator substance used at the time of calibration is not detected, it is regarded that there is no influence of the reagent indicator substance. The flow is ended.

If the reagent indicator substance is sensed in Step 12, it is determined that the chemical for the test is included in Step 14 and the fact that "chemical for test" is detected is displayed on the display device (not illustrated). The flow is ended.

In this manner, the peak 4 is set as the reagent indicator substance condition of the detection flow of FIG. 3 in the hazardous substance sensing device. As a result, even if the hazardous substance A is sensed, it can be determined that the hazardous substance A is the chemical for the test by sensing the indicator substance.

As another application example, an example used as a reference for cleaning after confirming the soundness of the device will be described. In a case where the spectrum of peak 4 is detected, it is determined that the chemical for the test remains. Therefore, physical cleaning such as heating temperature rise, air blowing, wiping off or the like is performed until the peak 4 disappears.

Example 2

Figure 4:
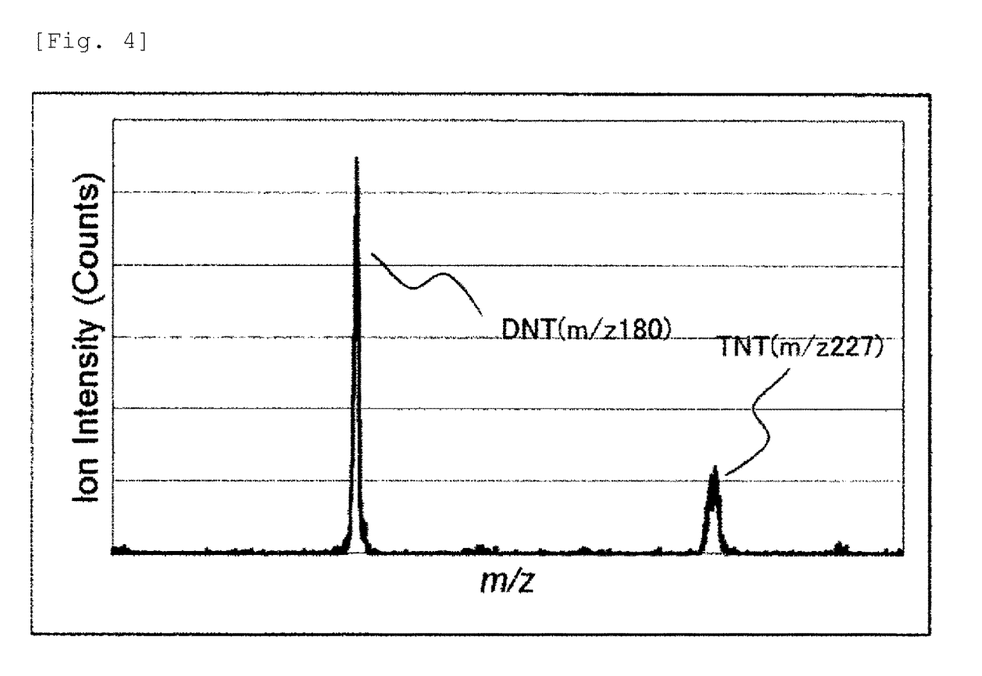
FIG. 4 is a graph illustrating an example of a mass spectrum graph of fine particles of a pseudo hazardous substance to which an indicator substance DNT is added.

An example when DNT (dinitrotoluene) is added as an indicator substance for Example 2 of the invention will be described. Differences from Example 1 will be described. Therefore, a portion in which the description is omitted is similar to Example 1. FIG. 4 is a graph illustrating an example of a mass spectrum graph of fine particles of the pseudo hazardous substance to which an indicator substance DNT is added, instead of the chemical for the test illustrated in FIG. 2. In the flow illustrated in FIG. 2, the following detection target (hazardous substance) and added substance (reagent indicator substance) are used. The fine particles of the pseudo hazardous substance illustrated in FIG. 4 contained 0.1% of TNT and 0.1% of DNT, and were prepared by injecting 200 μL of a DNT solution having a concentration of 0.1 μg/μL diluted with acetone and drying for 2 days, so that DNT has DNT content of approximately 0.1% based on the total amount with respect to 20 mg of silica gel having a particle diameter of 20 to 30 μm/piece, to which 0.1% of TNT (trinitrotoluene) is attached. When the fine particles of the pseudo hazardous substance to which DNT is added is measured with the trace type hazardous substance sensing device having a mass spectrometer, the peaks of two mass spectra are simultaneously measured, and DNT is simultaneously sensed for a regent that is sensed as TNT in the reagent alone of the fine particles of the pseudo hazardous substance. Therefore, it can be determined that the fine particles of the pseudo hazardous substance are being measured.

For a diluted solution of an additional indicator substance, acetone was used as an example this time. Alternatively, other solvents or mixed solvents such as methanol, acetonitrile, ethanol, hexane, or the like may be used. If other explosive particles such as RDX (hexogen) or PETN (pen slit) are used in the same manner as described above, it can be applied to other types of explosives. In addition, similar reagents can be prepared by adding an explosive solution to fine particles to which DNTs are attached rather than fine particles to which explosives are attached. Furthermore, after drying, it is dissolved again in a solvent such as acetone and dried again, so that it is likely to adhere to the silica gel. Silica gel is used this time. Alternatively, if it is possible to attach the reagent, it may be a solid or liquid such as glass beads, plastic beads, granules such as metal and ceramic. The indicator substance to be added may be a substance such as trichlorophenol (TCP) and tribromophenol (TBP) in addition to DNT, and any substance may be used as long as the substance in which the inspection target and the mass spectrum are not overlapped. By increasing the number of substances to be added to the reagent to multiple, the mass spectrum of the reagent indicator can be increased.

Figure 5:
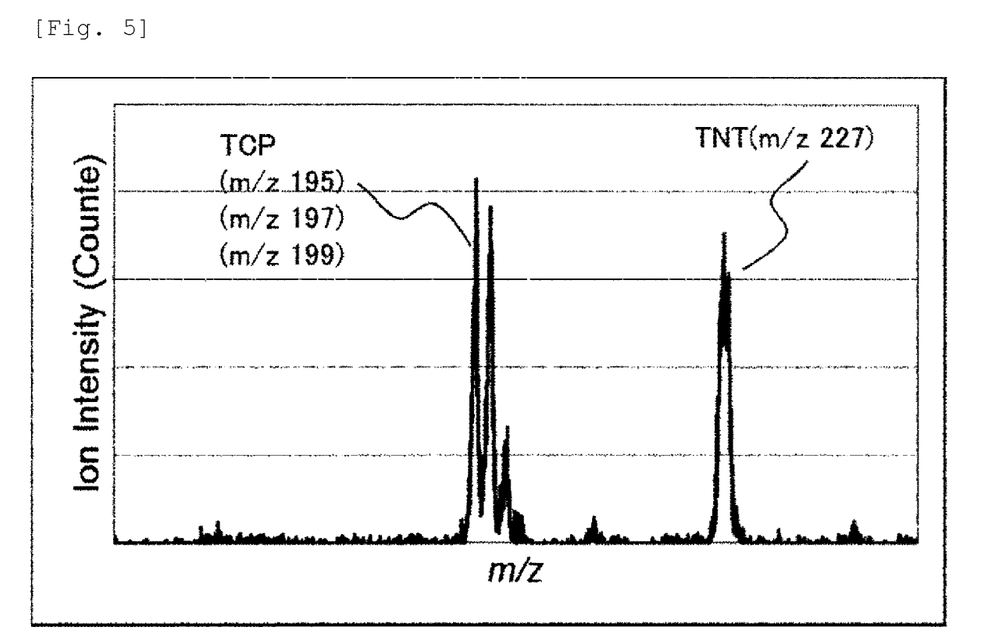
FIG. 5 is a graph illustrating an example of a mass spectrum graph of fine particles of a pseudo hazardous substance to which an indicator substance TCP is added.

FIG. 5 is a graph illustrating an example of a mass spectrum graph of the fine particles of the pseudo hazardous substance to which an indicator substance TCP is added. FIG. 5 illustrates a mass spectrum of the fine particles of the pseudo hazardous substance having 0.1% of TNT and 0.1% of TCP %, prepared by the same technique as DNT. Similarly to DNT, it is possible to determine that peaks of two mass spectra derived from an explosive and an indicator substance are simultaneously measured, and the fine particles of the pseudo hazardous substance are measured. Particularly, in a case where a plurality of peaks are detected as in TCP, it is more likely to determine that it is derived from the indicator substance. In the technique of adding the indicator substance, it is possible to add the indicator substance not only in a solid such as silica gel but also in a solution.

Example 3

Figure 6:
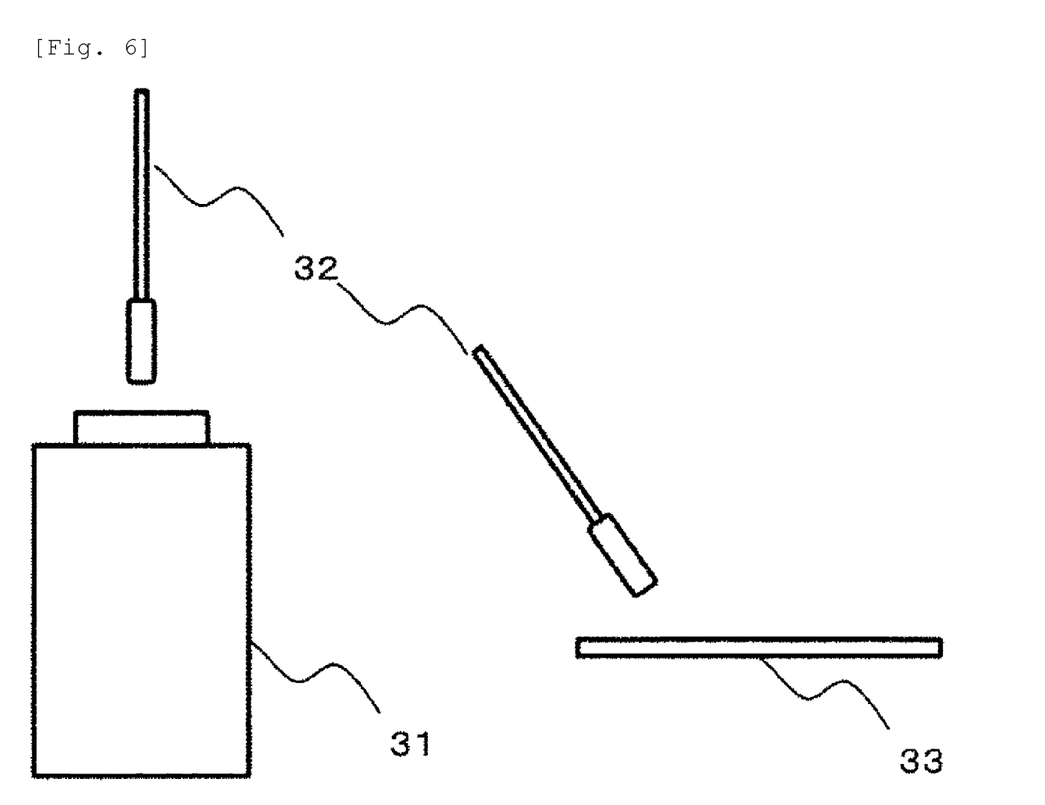
FIG. 6 is a diagram illustrating an example of a technique for attaching fine particles quantitatively on a card.

Example 3 is described. FIG. 6 is a diagram illustrating an example of a technique for attaching the fine particles quantitatively on a card. It is not easy to attach an amount that cannot be measured with an electronic balance or the like on the card. By using a technique of putting a cotton swab 32 in a container 31 containing the fine particles of the pseudo hazardous substance as illustrated in FIG. 6, attaching the fine particles of the pseudo hazardous substance to the tip end of the cotton swab 32, and attaching the cotton swab to the surface of the card 33 (used as inspection target 18 in FIG. 1) with the fine particles of the pseudo hazardous substance attached to the tip end thereof, the adhesion amount can be controlled by the area of the tip end of the cotton swab 32.

Figure 7:
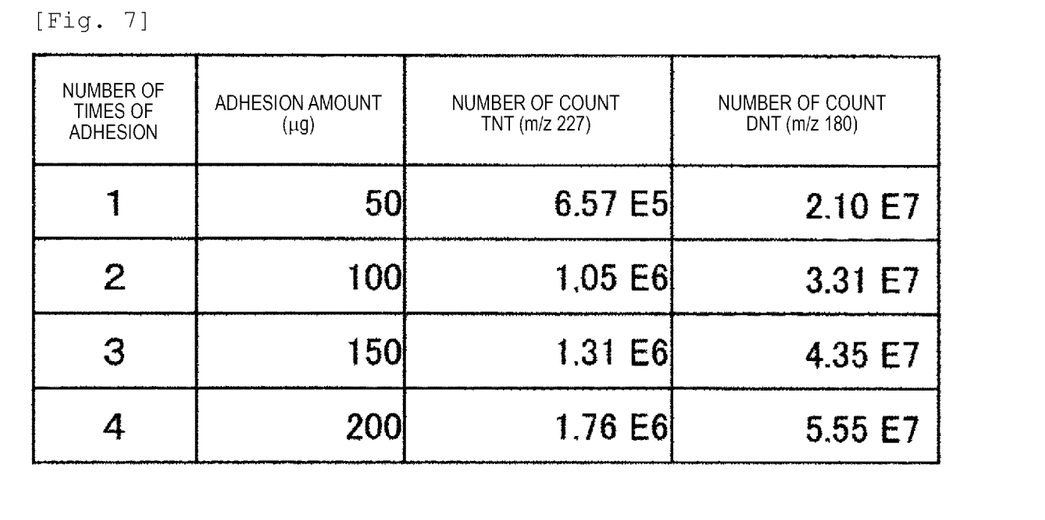
FIG. 7 is a table illustrating an example of the number of times the fine particles are attached to the card with a cotton swab and a mass spectrum intensity.

FIG. 7 is a table illustrating an example of the number of times the fine particles are attached to the card with a cotton swab and a mass spectrum intensity. FIG. 7 illustrates the adhesion amount and the signal intensity of the detected mass spectrum when the fine particles of the pseudo hazardous substance with TNT of 0.1% and DNT of 0.1% are attached to the card surface by the above-described technique using the cotton swab with a tip of Φ 2.0 and inspected by the device of FIG. 6. At this time, it can be understood that approximately 50 µg of fine particles containing approximately 50 ng of TNT and approximately 50 ng of DNT per one adhesion of the cotton swab are attached to the card, the adhesion number and the signal intensity of the mass spectrum are in a proportional relationship, and a certain amount of the fine particles of the pseudo hazardous substance of tens of micro order on the surface of the card 33 is attached. If the fine particles of the pseudo hazardous substance to be attached this time are the fine particles of the pseudo hazardous substance to which the indicator substance of the invention is added, since false alarms are not issued even if the fine particles of the pseudo hazardous substance adheres to the periphery of the device and erroneously enters during inspection at the time of operation, it is possible to prevent a decrease in throughput. In addition, description is made using the cotton swab of Φ 2.0 in the example. Alternatively, by changing the size of the cotton swab, the adhesion amount can be changed.

Figure 8:
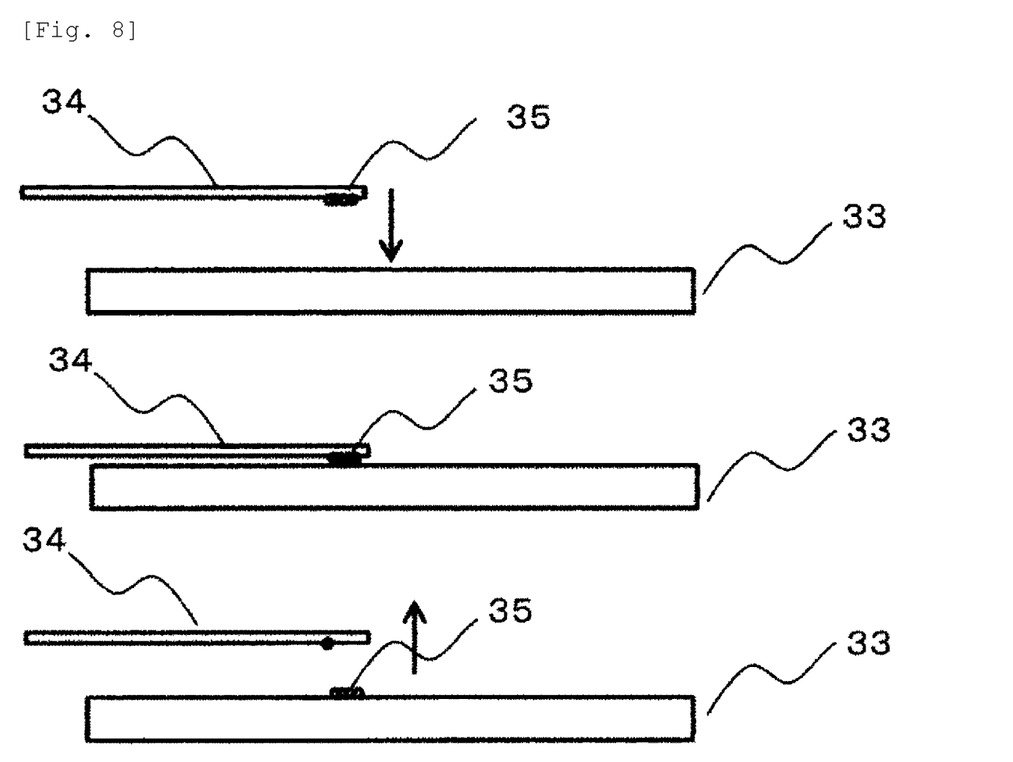
FIG. 8 is a diagram illustrating an example of a method of attaching the fine particles to the card.

FIG. 8 is a diagram illustrating an example of a method of attaching the fine particles to the card. Attachment to the inspection target with the cotton swab was described this time. Alternatively, by attaching the fine particles of the pseudo hazardous substance 35 to an adhesive one such as the seal 34 as illustrated in FIG. 8 and transferring to the card 33, it is possible to attach the fine particles of the pseudo hazardous substance 35 to the inspection target. In the example, the adhesion target is a card. Alternatively, the adhesion target may be attached to another inspection target such as a bag, a card holder, clothes, a hand or the like. In the example, the cotton swab is used. Alternatively, a portion having a controlled tip area such as metal, paper, wood, plastic, ceramic, adhesive material or the like may be used. In addition, the fine particles of the pseudo hazardous substance prepared with silica gel this time are described. Alternatively, a certain amount of other individual fine particles can be attached to the inspection target in the same manner.

Example 4

Figure 9:
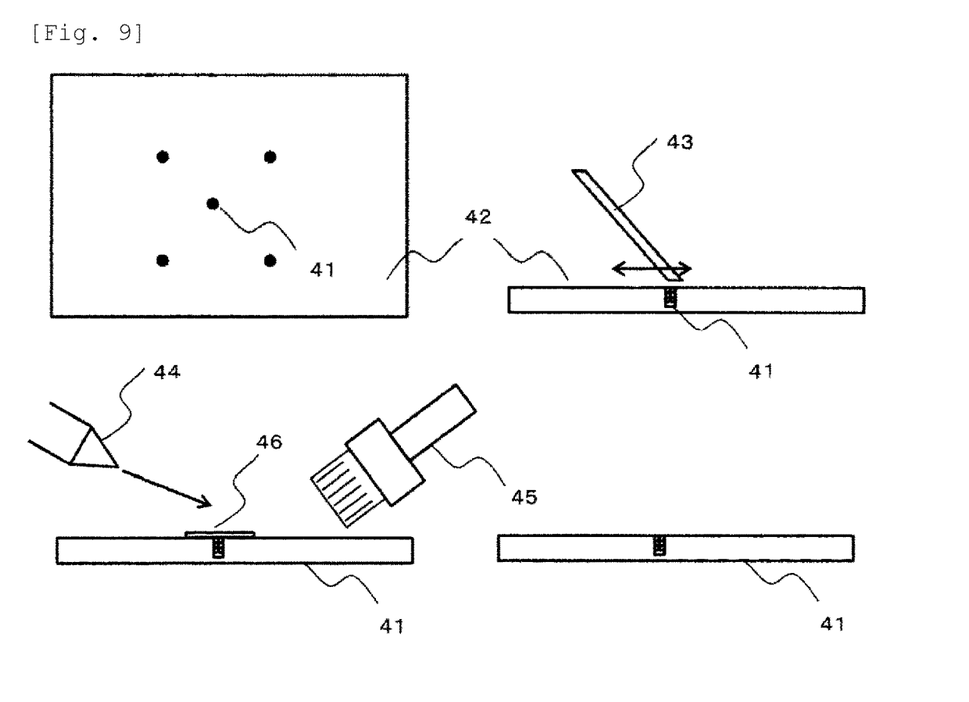
FIG. 9 is a diagram illustrating an example of a technique for quantitatively attaching the fine particles to the card.

An example of attaching quantitative fine particles to the inspection target for Example 4 of the invention will be described. FIG. 9 is a diagram illustrating an example of a technique for quantitatively attaching the fine particles to the card (used as inspection target 18 in FIG. 1). When the technique of Example 3 is used, it is possible to simply attach minute amounts of fine particles to the card. Alternatively, there are many variations in adhesion amount by the inspector, so that to use for sensitivity confirmation that requires quantitative evaluation, error is large and accuracy is poor. In order to solve this problem, the card holder 42 in which holes are opened as illustrated in FIG. 9 was used. As illustrated in FIG. 9, the card holder 42 is prepared in which one or a plurality of non-penetrating holes 41 are opened on the card surface. After filling the hole 41 with fine particles for inspection and eliminating excess fine particles with a spatula 43 or the like, the hole is closed with a lid 46 and extra fine particles on the card holder are cleaned with a brush 44, air 45 or the like around the periphery. As a result, since only the fine particles corresponding to the volume of the hole remain on the card holder 42, the amount of fine particles on the card can be set to a fixed amount, and quantitative sensitivity confirmation can be performed.

Figure 10:
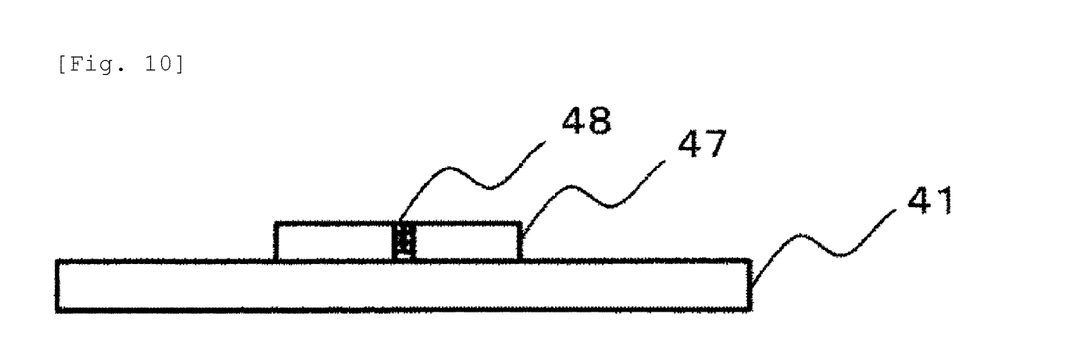
FIG. 10 is a diagram illustrating an example of a technique for quantitatively attaching the fine particles to the card.

FIG. 10 is a diagram illustrating an example of a technique for quantitatively attaching the fine particles to the card. In a case where it is difficult to prepare the card or the card holder in which the holes are opened, as illustrated in FIG. 10, a sheet 47 in which a hole 48 is opened may be pasted. The positions of the holes are also near the center in FIG. 9. Alternatively, the positions of the holes are not limited. The card holder is used as a description. Alternatively, the inspection target may be attached to another inspection target such as a bag or clothing.

Figure 11:
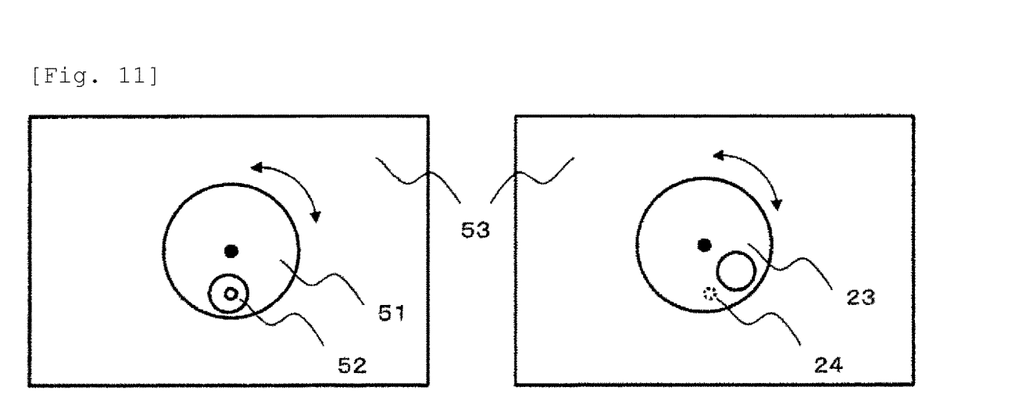
FIG. 11 is a diagram illustrating an example of a mechanism for quantitatively attaching the fine particles to the card.
Figure 12:
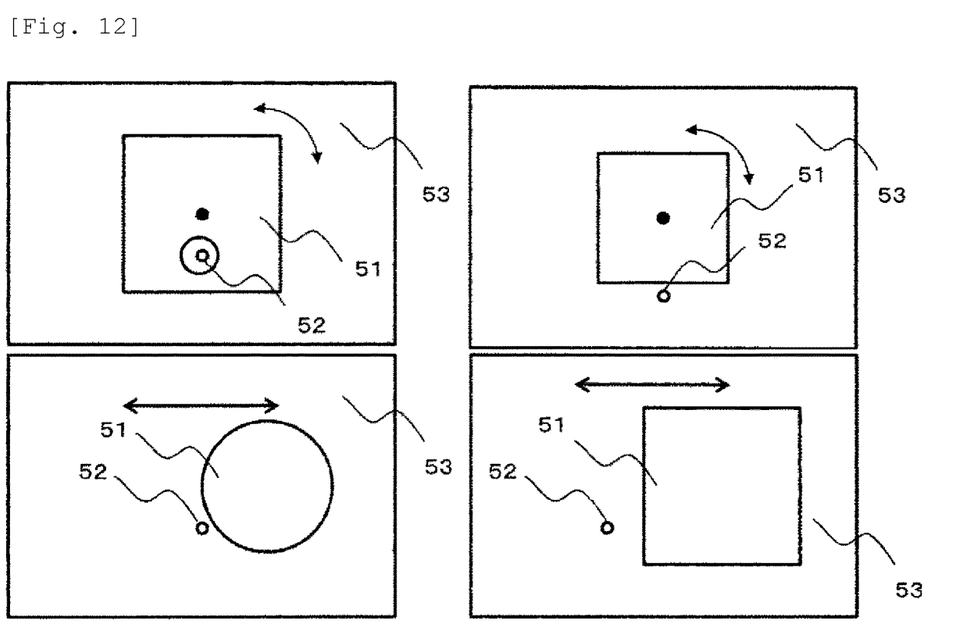
FIG. 12 is a diagram illustrating an example of a mechanism for quantitatively attaching the fine particles to the card.
Figure 13:
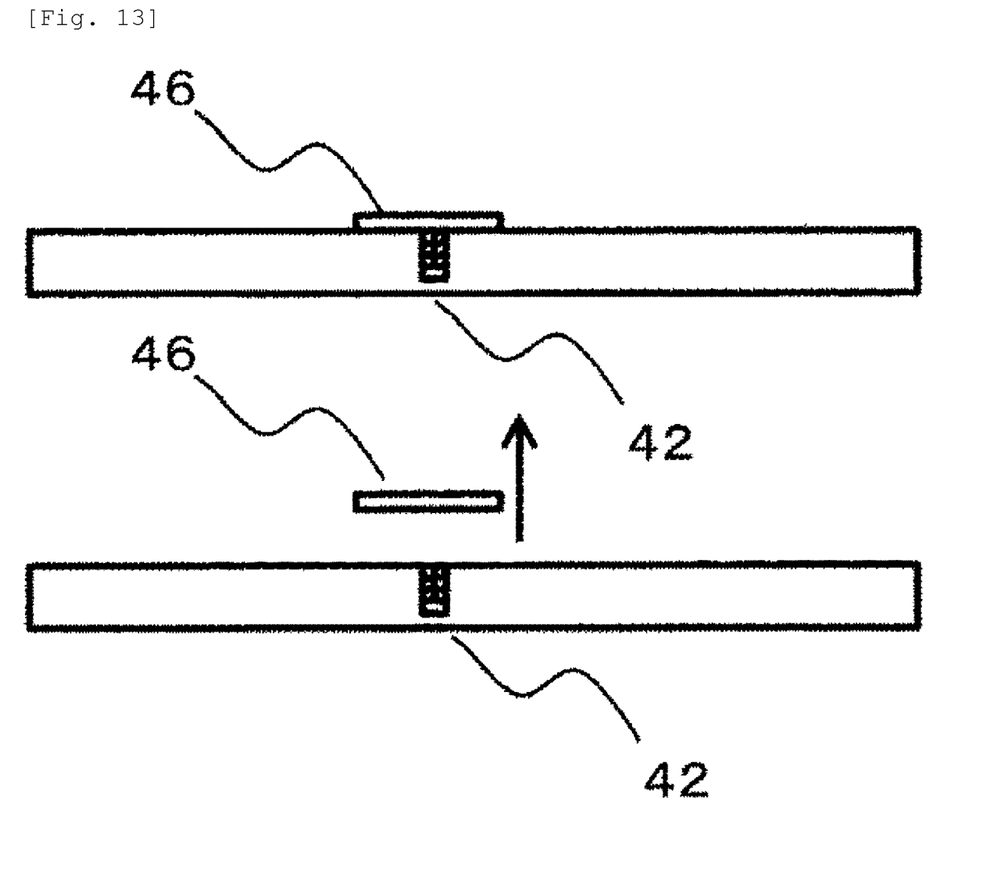
FIG. 13 is a diagram illustrating an example of a method of providing a jig to which the fine particles are attached.

In addition, FIG. 11 is a diagram illustrating an example of a mechanism for quantitatively attaching the fine particles to the card. If the structure is such that the hole 52 can be covered with a slide 51 as illustrated in FIG. 11, by sliding the slide 51, since an effect equivalent to that of the spatula 43 can be obtained and can be simultaneously covered, so that the work to be performed with the spatula and the lid can be simultaneously performed. FIG. 12 is a diagram illustrating an example of a mechanism for quantitatively attaching the fine particles to the card. In FIG. 11, a sliding mechanism is described as being in a shape of a circle. Alternatively, any shape such as square, rhombus or the like is acceptable, as long as the container is maintained as illustrated in FIG. 12. In FIG. 11, the slide in the rotation direction is used. Alternatively, it may be slid laterally or slid in the vertical direction as illustrated in FIG. 12, or the rotation shaft may not be at the center. In a case where it is difficult to drill a hole in the inspection target, a sheet may be stuck on the surface of the inspection target as described above. In addition, in a case where it is difficult to fill the reagent fine particles at the inspection site, by previously filling the fine particles and previously covering with a sheet or the like as the lid 46 as illustrated in the figure illustrating an example of a method of providing a jig to which the fine particles are attached in FIG. 13, the inspection can be performed on the spot even in an environment where it is difficult to fill the fine particles.

The invention is not limited to the embodiments described above and it goes without saying that various other applications and modifications can be made without departing from the gist of the invention described in the aspects.

For example, the above-described embodiment describes the mass spectrum and the detection flow in detail and concretely in order to describe the invention easily, and it is not necessarily limited to those having all the configurations described. In addition, it is possible to replace a portion of the configuration of one Example with the configuration of another Example. Furthermore, the configuration of another Example can be added to the configuration of one Example. In addition, it is also possible to add, delete, and replace other configurations with respect to a portion of the configuration of each Example.

REFERENCE SIGNS LIST

1 mass spectrum of hazardous substance
2 mass spectrum of hazardous substance
3 mass spectrum of hazardous substance
4 mass spectrum of indicator substance
10 start of measurement
12 presence or absence of hazardous substance sensing
13 presence or absence of indicator substance sensing
14 reagent sensing
15 hazardous substance sensing
16 absence of hazardous substance
17 air supply unit
18 inspection target
19 authentication unit
20 suction unit
21 collection unit
22 ion source unit
23 mass analysis unit
24 calibrant generator
31 container
32 cotton swab
33 card
41 reagent filling hole
42 card holder
43 spatula
44 air supply unit
45 spatula
46 lid
47 sheet
48 reagent filling hole
51 sliding mechanism
52 reagent filling hole
53 inspection target

The invention claimed is:

1. A hazardous substance sensing device using a reagent chemical to which an indicator substance different from a hazardous substance as a detection target is added and calibrated based on the detection target included in the reagent chemical, the device comprising:
    an analysis unit performing mass analysis; and
    a determination unit, the determination unit being configured to detect the indicator substance and the detection target during a determination unit calibration test, and the determination unit being further configured to determine, during analysis of a sample to which the indicator substance has not been added, that the detection target is included when a peak corresponding to the indicator substance is not included and a peak corresponding to the detection target is included in a spectrum as an analysis result of the analysis unit.

2. The hazardous substance sensing device according to claim 1, further comprising:
    a fine particle collection unit for collecting the substance as the detection target and the reagent indicator substance.

3. The hazardous substance sensing device according to claim 1,
    wherein fine particles are used as the reagent indicator substance.

4. The hazardous substance sensing device according to claim 1,
    wherein the analysis unit is configured to include any one of a linear ion trap mass spectrometer, a quadrupole ion trap mass spectrometer, a triple quadrupole mass spectrometer, a time-of-flight type mass spectrometer, a magnetic field type mass spectrometer, and an ion mobility mass spectrometer.

5. The hazardous substance sensing device according to claim 1,
    wherein the reagent indicator substance is supplied by being attached to a jig capable of holding the reagent indicator substance in a certain area.

6. The hazardous substance sensing device according to claim 1,
    wherein the reagent indicator substance is supplied by being attached to a jig capable of holding a volume of the reagent indicator substance.

7. The hazardous substance sensing device according to claim 6,
    wherein a lid is provided on the jig.

8. A hazardous substance sensing method comprising:
    using a reagent chemical to which an indicator substance different from a hazardous substance as a detection target is added and performing calibration based on the detection target included in the reagent chemical;
    performing mass analysis;
    detecting the indicator substance and the detection target during the calibration; and
    determining, during analysis of a sample to which the indicator substance has not been added, that the detection target is included, in a case where a peak corresponding to the indicator substance is not included and a peak corresponding to the detection target is included in a spectrum as an analysis result.

* * * * *